(12) United States Patent
Kavsek et al.

(10) Patent No.: US 10,401,275 B2
(45) Date of Patent: Sep. 3, 2019

(54) ANALYSIS METHOD FOR SUPPORTING CLASSIFICATION

(71) Applicant: Siemens Healthcare Diagnostics Products GmbH, Marburg (DE)

(72) Inventors: Barbara Kavsek, Sankt Radegund bei Graz (AT); Peter Lederer, Graz (AT); Peter Taal, HK Oost-Souburg (NL); Jan van den Boogaart, AG Someren (NL)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 217 days.

(21) Appl. No.: 14/912,876

(22) PCT Filed: Aug. 5, 2014

(86) PCT No.: PCT/EP2014/066786
§ 371 (c)(1),
(2) Date: Mar. 3, 2016

(87) PCT Pub. No.: WO2015/024770
PCT Pub. Date: Feb. 26, 2015

(65) Prior Publication Data
US 2016/0202171 A1 Jul. 14, 2016

(30) Foreign Application Priority Data
Aug. 19, 2013 (DE) .................. 10 2013 216 362

(51) Int. Cl.
*G01N 15/14* (2006.01)
*G01N 33/49* (2006.01)
(Continued)

(52) U.S. Cl.
CPC ......... *G01N 15/1456* (2013.01); *G01N 21/49* (2013.01); *G01N 33/49* (2013.01);
(Continued)

(58) Field of Classification Search
CPC ....... G01N 15/1456; G01N 2015/0073; G01N 2015/1006; G01N 2015/1477;
(Continued)

(56) References Cited

U.S. PATENT DOCUMENTS

2003/0017481 A1 1/2003 Golub et al.
2007/0231206 A1* 10/2007 Nagai .................... G01N 15/12
422/63

(Continued)

FOREIGN PATENT DOCUMENTS

CN 1371660 A 10/2002
CN 1653480 A 8/2005
(Continued)

OTHER PUBLICATIONS

Chinese Search Report of Chinese Application No. 2014800457693 dated Nov. 14, 2017.
(Continued)

*Primary Examiner* — Violeta A Prieto
(74) *Attorney, Agent, or Firm* — Dugan & Dugan, PC (57) ABSTRACT

The invention relates to an analysis method for supporting classification, a determination method for determining analysis parameters $Y_s$, $E_i$, $I_i$, $\sigma_i$ for the analysis method, a computer program product, and an optical analysis system for supporting classification, with which system analysis parameters $Y_s$, $E_i$, $I_i$, $\sigma_i$ can be defined on the basis of first and second calibration data. The parameters provide classification support according to the discriminant analysis and on the basis of measured values $P_i$ of optical characteristics i, in particular of organic dispersions, and the information content thereof for classification, in particular the diagnosis of disease; and permit a classification proposal or a diagnosis proposal in comparison with a threshold $Y_s$.

19 Claims, 4 Drawing Sheets

US 10,401,275 B2

Page 2

(51) Int. Cl.
*G01N 21/49* (2006.01)
*G01N 15/00* (2006.01)
*G01N 15/10* (2006.01)
*G01N 21/47* (2006.01)

(52) U.S. Cl.
CPC ........ *G01N 2015/0073* (2013.01); *G01N 2015/1006* (2013.01); *G01N 2015/1477* (2013.01); *G01N 2015/1488* (2013.01); *G01N 2015/1497* (2013.01); *G01N 2021/4702* (2013.01); *G01N 2021/4769* (2013.01); *G01N 2800/22* (2013.01); *G01N 2800/26* (2013.01)

(58) Field of Classification Search
CPC ... G01N 2015/1488; G01N 2015/1497; G01N 2021/4702; G01N 2021/4769; G01N 21/49; G01N 2800/22; G01N 2800/26; G01N 33/49
See application file for complete search history.

(56) References Cited

U.S. PATENT DOCUMENTS

| | | | |
|---|---|---|---|
| 2008/0186490 A1* | 8/2008 | Chu | G01N 15/1434 356/338 |
| 2010/0248247 A1* | 9/2010 | Kataoka | G01N 33/49 435/6.1 |
| 2010/0273168 A1 | 10/2010 | Krockenberger et al. | |
| 2011/0172514 A1 | 7/2011 | Lee et al. | |
| 2011/0178716 A1 | 7/2011 | Krockenberger et al. | |
| 2011/0306849 A1* | 12/2011 | Cales | A61B 5/416 600/301 |
| 2012/0115159 A1* | 5/2012 | Kono | G01N 15/1459 435/6.19 |
| 2012/0164684 A1* | 6/2012 | Nagai | G01N 15/12 435/39 |
| 2012/0244573 A1* | 9/2012 | Nagai | G01N 15/12 435/39 |
| 2012/0282601 A1* | 11/2012 | Abe | G01N 35/026 435/6.1 |
| 2013/0337496 A1* | 12/2013 | Hayden | C12Q 1/02 435/34 |
| 2014/0011232 A1* | 1/2014 | Vidal | C12Q 1/06 435/39 |
| 2014/0051071 A1* | 2/2014 | Yoshida | G01N 21/51 435/6.1 |
| 2016/0202170 A1* | 7/2016 | Yoshida | G01N 21/51 435/34 |

FOREIGN PATENT DOCUMENTS

| | | |
|---|---|---|
| CN | 101059431 A | 10/2007 |
| CN | 101716069 A | 6/2010 |
| CN | 102933964 A | 2/2013 |
| DE | 19737109 A1 | 3/1998 |
| DE | 10317717 A1 | 11/2004 |
| EP | 2280278 A1 | 2/2011 |
| JP | 2006501528 A | 1/2006 |
| JP | 2012525589 A | 10/2012 |
| WO | WO 0058727 A1 | 10/2000 |
| WO | WO 2009136570 A1 | 11/2009 |
| WO | WO 2013093913 A1 | 6/2013 |

OTHER PUBLICATIONS

Japanese Office Action of Japanese Application No. 2016-535396 dated Apr. 3, 2018.

* cited by examiner

ANALYSIS METHOD FOR SUPPORTING CLASSIFICATION

CROSS REFERENCE TO RELATED APPLICATIONS

This is a U.S. National Phase of International Patent Application No. PCT/EP2014/066786, filed Aug. 5, 2014, which claims priority to German Patent Application No. DE 10 2013 216 362.2, filed Aug. 19, 2013, both of which are hereby incorporated by reference herein in their entireties for all purposes.

FIELD

The invention relates to an analysis method for classification assistance, an ascertainment method for determining parameters of the analysis method, and a computer program product, as well as an optical analysis system.

BACKGROUND

In the medical field, optical analysis systems and optical methods are used to optically analyze organic dispersions, which consist, on the one hand, of a dispersion medium and, on the other hand, of a dispersed phase. The dispersed phase generally comprises particles, in particular organic material, for example, cells or cell components. The dispersion medium can be understood as media which comprise the dispersed phase, dilute it, or receive it in another manner, for example, blood plasma.

The analysis of the components of a dispersion can be carried out using optical methods, wherein a light beam, in particular a laser beam, is focused in the dispersion and subsequently examined for various optical features. In this manner, measured values for specific features of the dispersion can be ascertained.

An analysis system is known from WO 00/58727, which consists of a light source, the light of which is focused in a dispersion circulation unit (flow cell) and is subsequently analyzed. The analysis relates in particular to the spectral ascertainment of the wavelengths of the light used which are absorbed in the dispersion. On the other hand, the diffraction characteristics in the near field and the far field are documented, to infer specific properties of the dispersion, in particular the particles contained in the dispersion, for example, the red blood cells, the white blood cells, or blood platelets. An optical, hematological examination, as is known from the prior art, can advantageously be performed in an automated manner, wherein an array of optical features of the dispersion are examined. However, the optical analysis method limits the information content which is extractable for the dispersion. Although items of information can be obtained on the absorption behavior or frequency values of white and red blood cells or blood platelets, the extracted information content is still inadequate for carrying out many medical diagnoses.

For example, in the case of the malaria diagnosis, a blood sample of the patient cannot be automatically examined as a dispersion, but rather must be examined manually under the microscope in the laboratory. The present best method (the gold standard) for the malaria diagnosis is the blood smear on a slide or between two slides. Malaria parasites are detected by light microscopy by means of thin and thick blood smears. The accuracy of the diagnosis is dependent to a large extent on the quality of the blood smear and the experience of the laboratory personnel.

A special ring shape, which can be recognized under the microscope, is characteristic for red blood cells infected by parasites, however, a reliable diagnosis is only ensured if a sufficient number of these ring-shaped red blood cells can be counted in the dispersion of the blood sample. On the basis of this counting experiment, a physician can recognize whether it is a severe or less severe malaria infection. Unfortunately, counting the ring-shaped red blood cells under the microscope is very boring, cumbersome, and subject to error, so that a malaria diagnosis is costly and excessively inaccurate. In addition, various laboratories refer in various notations to different ranges with respect to the counted ring-shaped red blood cells. In this manner, the question also arises of how a standardized, dependable malaria diagnosis or also diagnoses of other illnesses or negative states can be carried out reliably.

SUMMARY

The invention is based on the object of providing an optical analysis method, which improves the information content of an optical analysis method such that more precise statements are possible on the dispersion, in particular diagnoses and classifications.

This object is achieved according to the invention by an analysis method for classification assistance as claimed in claim 1, an ascertainment method for determining analysis parameters of the analysis method as claimed in claim 7, a computer program product as claimed in claim 13, and an optical analysis system as claimed in claim 14.

According to the invention, the analysis method for classification assistance includes the following steps:

ascertaining measured values ($P_i$) for optical features of a test dispersion to be classified, wherein the test dispersion is formed from a dispersion medium, in particular blood plasma, and a dispersed phase and the dispersed phase has cells or cell components, in particular organic materials, calculating a classification index Y, defined by:

$$Y = \sum_{i=1}^{n} l_i * (P_i - E_i)/\sigma_i,$$

wherein the classification index Y is dependent on a number n of the optical features i of the test dispersion, a significance parameter $l_i$ of the respective optical feature i, a mean value $E_i$ of the respective optical feature i, and a standard deviation $\sigma_i$ of the respective optical feature i.

The classification index is provided for the purpose of giving information which enables a classification to be performed for a dispersion, in particular an organic dispersion. The classifications can originate in this case from various fields of medicine, technology, or from probability theory or from similar fields. Possible classifications are, for example, the presence or the absence of an illness, equally also the presence or the absence of a property, which is to be understood in the most general meaning. In this case, the number of classes is equally not restricted much, nor is the technical field thereof, thus, two, three, or multiple classification alternatives can be possible and can be indicated by the classification index.

In addition, the classification by the classification index is to be considered to be a proposal, which is correct at a specific probability, but does not necessarily have to be present. It is therefore possible that the classification index proposes a classification of the dispersion, but this proposal does not apply with respect to the individual case at a specific, ideally low probability.

A dispersion medium is understood as a medium, in particular a liquid medium, which is capable of receiving the dispersed phase such that the cells or cell components associated with the dispersed phase can also be transported by a movement of the dispersion medium. For example, it is advantageous in the case of a test dispersion to be classified, for example, a blood sample, to keep it in a flowing state during the optical ascertainment of measured values for the optical features. In this manner, it is possible, on the one hand, to ensure thorough mixing of the test dispersion, which is required for statistical consideration, or alternatively to avoid intrinsically caused changes of the dispersion, for example, a coagulation in the event of blood dispersions.

The classification index is dependent on a number of the optical features of the test dispersion. A measured value is to be assigned to an optical feature of the test dispersion, whereby a specific information content of the test dispersion can be inferred by the measurement of the assigned measured value. An optical feature can be, for example, a number of specific cells, for example red blood cells, white blood cells, or the like, within a specific volume unit. However, it can also be an optical feature on the shape or absorption characteristic of the mentioned cells. This feature list is not exhaustive.

The optical features per se do not enable an unambiguous classification, indexing, or diagnosis, so that a single optical feature hardly provides any valuable items of information. However, optical features nonetheless bear a certain significance per se with respect to a classification. To obtain an assistance for a classification, it is advantageous to select a number of specific optical features, which can contain a certain significance for this classification. In dependence on the respective classification problems of an embodiment, technical backgrounds or technical prior knowledge can be used for the selection of the optical features, the measured values of which can then be used as the basis for the analysis method for the classification assistance. These fundamental optical features are also referred to hereafter as a feature set. For example, in the case of a blood sample of a test dispersion, in the case of a malaria diagnosis assistance, the optical features are used which occur in conjunction with red blood cells. This can be established by prior knowledge, which originates from the conventional microscope-based diagnosis assistance, in which red blood cells are also examined. However, other optical features which relate to other components of the test dispersion can gradually be added to the feature set or features already associated with the feature set can be removed based on the significance of the information content. Thus, it can prove that an optical feature, although it relates to the red blood cells, has no informative power with regard to malaria and can therefore be removed from the feature set. Vice versa, an optical feature which relates to a cell, for example, which interacts with the red blood cells, and therefore also plays a role in a parasitic malaria infestation, can contribute via the corresponding optical feature such that its significant information content is provided for the analysis method for classification assistance, in that the optical feature is taken into consideration for a malaria diagnosis assistance.

A significance parameter is assigned in each case to an optical feature, wherein it can indicate by its absolute value and/or its sign to what extent the measured value of the respective optical feature has an effect on the classification index. Furthermore, a ranking can be established on the basis of the significance parameter, on the basis of which the importance of the feature for a classification, diagnosis, or the like is shown. On the basis of the significance parameter, it is also possible to recognize whether the measured value of an optical feature should advantageously still be used in the feature set for the analysis method for classification assistance. One goal of the analysis method for classification assistance is the most accurate possible determination of the significance parameters for the optical features to be identified as important.

Furthermore, the classification index is dependent on mean values, wherein the individual mean values can each be assigned to optical features. The mean values are mean values of measured values of the respective optical feature which are obtained from calibration data. The classification index is dependent in particular on the difference of the ascertained measured value of the test dispersion and the mean value for the optical feature, whereby the ascertained measured value influences the classification index more strongly the more remote it is from the mean value.

Furthermore, the classification index is dependent on the standard deviation of the respective optical feature, whereby a scaling is achieved which takes into consideration a natural variance of the measured value of the optical feature to be considered, and therefore the natural variance of the measured value cannot influence the classification index, wherein simultaneously no imbalance results between the summands of the sum in the classification index formula.

In one advantageous embodiment of the analysis method for classification assistance, the mean value of the optical feature and the standard deviation of the measured value of the optical feature have been ascertained on the basis of first calibration data, wherein the first calibration data are derived from dispersions having a negative classification, in particular are derived from the first and second calibration data, wherein the second calibration data are derived from dispersions having positive classification. In this embodiment, only two classes are provided for the classification. For example, in an analysis method for classification assistance in illness diagnoses, a statement is simply required as to whether the test dispersion originates from a sick patient or from a healthy patient. Therefore, the mean values of measured values of a specific optical feature are considered with regard thereto, with the previous knowledge of whether the test dispersion is to be assigned to a positive classification or a negative classification. For example, the mean value can be formed using measured values of the optical feature in which a negative classification is known. In the case of illness diagnoses, this would correspond to a certain extent to a calibration using a mean value of healthy patients. Therefore, the deviation of the measured value of the test dispersion from this mean value is evaluated as the information content, which has relevance with regard to the classification. If the ascertained measured value of the test dispersion is very close to the mean value or is even identical thereto, the associated optical feature thus does not provide a contribution.

The first calibration data can be derived from dispersions of negative classification, but also alternatively from dispersions having a positive classification. The second calibration data are therefore associated in each case with the classification different from that of the first calibration data.

In principle, calibration data are ascertained from measured values of optical features measured on dispersions, which were ideally established with a large variety of dispersions, to ensure a statistical informative power which is required for optimum classification assistance. These calibration data can have been ascertained by means of classification methods of the prior art, for example in the case of malaria diagnosis, by means of blood smears and the microscopic evaluation thereof. Furthermore, the classification data should be based on a sufficient number of dispersions of different classifications, ideally an essentially equal number of data sets for the respective classification.

The significance parameters are advantageously derived from the first and from the second calibration data by means of a discrimination analysis, wherein in particular a Bayesian theory is used in the discrimination analysis.

In the discrimination analysis, the classification index is interpreted as a random variable, wherein a probability of the presence of a classification can be plotted over the frequency of the classification index. In this manner, the classification index supplies a probability distribution, which contains both test dispersions having positive and also negative classification, or generally, using all provided classifications. The discrimination analysis describes how decisions, which result in an accurate classification, are to be made on the basis of the probability distribution over the classification index.

In one special embodiment, a classification rule can be specified, on the basis of which value ranges of the classification index can be assigned to a specific classification. In the special case of the two-class classification (positive/negative, good/bad, minus/plus), a threshold value can also be specified for the classification index, which divides the value range of the classification index into two intervals and therefore also results in a classification rule. In the exemplary embodiment of the illness diagnosis, if the value falls below the specified threshold value, a negative diagnosis can be proposed, and if the threshold is exceeded, a positive diagnosis can be proposed.

For example, the Bayesian theory can be used, wherein prior and posterior probability can also be incorporated into the calculation. In this case, sufficient knowledge or calibration data of reliable prior probabilities has to be provided, so that the theory comes to bear. In this case, probabilities which are estimated with previous knowledge are considered to be prior probabilities and probabilities which were calculated afterwards are considered to be posterior probabilities. In this case, the distance of the focal points to the test data is to be taken into consideration.

In one advantageous embodiment, the mean value of the measured value of an optical feature is the arithmetic mean of multiple measured values of first and/or second calibration data. Alternatively, the mean value of a measured value for an optical feature can also be a focal point of a group of points in one-dimensional or multidimensional space.

Preferably, based on a mean classification index, in particular a first focal point, of the first calibration data and a mean classification index, in particular a second focal point, of the second calibration data, a threshold value is usable for the classification assistance, wherein a positive classification exists if the classification index is greater than the threshold value and a negative classification exists if the classification index is less than the threshold value. The threshold value can be selected as a function of the mean classification index, wherein the threshold value can be, for example, the arithmetic mean of the two mean classification indices. However, the threshold value can also be based on the variance of classification indices, which can vary more or less strongly as a function of the classification. Fundamentally, the ascertainment of the threshold value can take place on the basis of the discrimination analysis. For example, the threshold value can be established between the two mean classification indices such that positive and negative classification is equally probable at the threshold value.

In one advantageous embodiment, a positive classification indicates a presence of a deficiency, a parasitic infestation, or a nonnormal state, wherein the deficiency is in particular an anemia, in particular a Mediterranean anemia or a sickle-cell anemia, and wherein the parasitic infestation is in particular leishmaniasis or another parasitic infection. The mentioned presence of a deficiency, a parasitic infestation, or a nonnormal state can always be assigned to the test dispersion, so that a statement or diagnosis on the test dispersion is possible.

At least two optical features are advantageously taken into consideration for the calculation of the classification index:

$$Y(n=2)=l_1*(P_1-E_1)/\sigma_1+l_2*(P_2-E_2)/\sigma_2,$$

wherein n=2 and a first optical feature is a measure of optical scattering in a transverse X direction in relation to an analysis beam and a second optical feature is a measure of optical scattering in a Y direction, which is perpendicular to the X direction and also perpendicular to the analysis beam, wherein the analysis beam extends through the test dispersion. With a higher number n, the number of the summands of the classification index Y also increases accordingly. A balance can always be made between computing effort and additional information content in the selection of the number.

In dependence on the individual case, the feature set can be selected to be very small, i.e., only a few, ideally two optical features are sufficient to propose a classification reliably enough. The measured values of the optical features which are used for the calculation of the classification index are advantageously also relevant for the classification, wherein the classification index is formed from a sum, the number of the summands of which corresponds to the number of optical features used.

The analysis beam advantageously extends essentially in a Z direction, which is perpendicular to both the X direction and also the Y direction. In the Z direction, the analysis beam can have been focused, defocused, or conditioned in another manner, for example by optical lenses, optical filters or the like, to have an optimum beam diameter in the test dispersion. After the transmission through the test dispersion, the analysis beam is analyzed, wherein, for example, near field scattering, far field scattering, and/or wavelength absorptions can be taken into consideration in the meaning of a spectral analysis.

The invention furthermore includes an ascertainment method for determining analysis parameters of the analysis method according to the invention, wherein for an established number of optical features, the analysis parameters of the standard deviation, the mean value, and the significance parameter are ascertained based on the first and/or the second calibration data. In this case, it is not always necessary for all types of analysis parameters to be subjected to an adaptation or ascertainment. For example, it is conceivable that the mean values, for example, as focal points, are formed from measured values, which are obtained from calibration data, of the respective optical features. This applies accordingly to the associated standard deviations of the measured values obtained from the first and/or the second calibration data.

At least the significance parameters have to be varied in the ascertainment method to optimize the classification assistance, in order to establish a weighting of the summands of the classification index such that a classification is as unambiguous as possible. This is precisely the case if value ranges of the classification index, which are each to be assigned to a classification, do not overlap with one another. A non-overlap will occur extraordinarily rarely in practice, but optimization is to be performed so that the mentioned value ranges overlap as little as possible.

At least one control parameter, in particular a measure of the overlap of the above-mentioned value ranges, is advantageously calculated based on the analysis parameters, in particular based on the significance parameters, to evaluate the classification assistance. The classification assistance is better the more the value ranges of different classifications are separated from one another, or the less they overlap.

Advantageously, at least a part of the analysis parameters is adapted after an evaluation by a first control parameter, wherein in particular an adaptation of the at least one analysis parameter and the evaluation of the classification assistance are to be executable alternately until an improvement is no longer possible or is no longer desirable. The present first and second calibration data always result, upon the variation of the analysis parameters or a part of the analysis parameters, in a different probability distribution of the classification index of the mentioned calibration data. Ideally, first and second calibration data are to demonstrably result in separable probability density distributions of different classifications. The first control parameter could be, for example, a minimum between the mentioned distributions, wherein the first control parameter always becomes smaller as much as possible during the progressive adaptation of the analysis parameters or the part thereof, so that a separation of the two distributions results more and more clearly. Other first control parameters can also be selected, which are ascertained, for example, by separate curve fits of the mentioned probability distributions. Multiple first control parameters can also play a role in this case, wherein they are obtained from the fit parameters, or are simply identical to one or more of the fit parameters.

The at least one part of the analysis parameters are/is advantageously the significance parameters and/or the threshold value. Fundamentally, the part of the analysis parameters to be adapted does not have to be identical to one type of analysis parameters, for example significance parameters, standard deviation, or mean value, but rather can also include parameters of different types. The threshold value can also be adapted to the probability distribution of the classification index, if distribution functions stand out for the distributions of different classifications, which can have effects on the threshold value.

In one advantageous embodiment, the ascertainment method or the analysis method is executable again using a reduced number of optical features as soon as an improvement is no longer possible, or is no longer desired, in consideration of the first control parameter, wherein the analysis parameters of one nonsignificant optical feature or multiple nonsignificant optical features are no longer taken into consideration, wherein a lack of significance of an optical feature is determined on the basis of the respective significance parameter. Since it is usually not known beforehand which measured values of optical features could actually contribute to the informative power of the classification index, for example, a large number of measured values of optical features can be taken into consideration at the beginning—ideally all available measured values, wherein measured values of optical features can gradually be excluded by the ascertainment method, because they have no or only a very small contribution to the informative power of the classification index. The significance parameter is decisive in this case, which indicates a significance if it is clearly not equal to zero.

Significance parameters which are very small and/or are nearly zero, can optionally also result in the exclusion of the measured value of the respective optical feature. In this manner, on the one hand, the informative power of the classification assistance is improved, on the other hand, as a result of the nonconsideration, the computing effort of a computer, on which, for example, the ascertainment method is implemented as a computer program, has to apply less computing power.

A lack of significance preferably exists if the influence of the optical feature on the classification index is small or does not exist. Nonetheless, measured values of various optical features can be omitted, if measured values of other optical features have sufficient information content. In this case, it is conceivable, for example, to begin with one feature set, which is comparatively small, and successively to add further measured values of other optical features to the feature set, whereby it can be tested in the individual case as to whether an improvement of the classification assistance has been achieved.

Furthermore, the subject matter of the invention is a computer program product, which makes a computer capable of executing the analysis method according to the invention and/or the ascertainment method according to the invention. For this purpose, it is advantageous if the first and/or second calibration data are provided to the computer in a suitable manner as data sets, so that the analysis parameters can be ascertained on a computer-implemented basis. It is advantageous in particular if comparative data exist, which were not used for the calibration, but on the basis of which the analysis method can be tested for its classification assistance.

The computer program product, in particular compact disks or the like, can advantageously contain an installable algorithm. The algorithm executes program loops having corresponding abort condition, which both can be used for ascertaining analysis parameters and also can be used for eliminating analysis parameters.

The subject matter of the invention is also an optical analysis system, in particular a hematological analysis system, having an analysis unit for carrying out an optical measured value recording of measured values, which can be assigned to optical features of the test dispersion. Such systems represent, for example, hematological analysis devices, which automatically ascertain an entire array of various measured values, which are assignable to optical features. The number of automatically ascertained measured values can be from several hundred up into the thousands, for example 1000 or 2000.

Further advantageous embodiments and preferred refinements of the invention can be inferred from the description of the figures and/or the dependent claims.

BRIEF DESCRIPTION OF THE DRAWINGS

The invention is described and explained in greater detail hereafter on the basis of the exemplary embodiments illustrated in the figures. In the figures.

DETAILED DESCRIPTION

Figure 1:
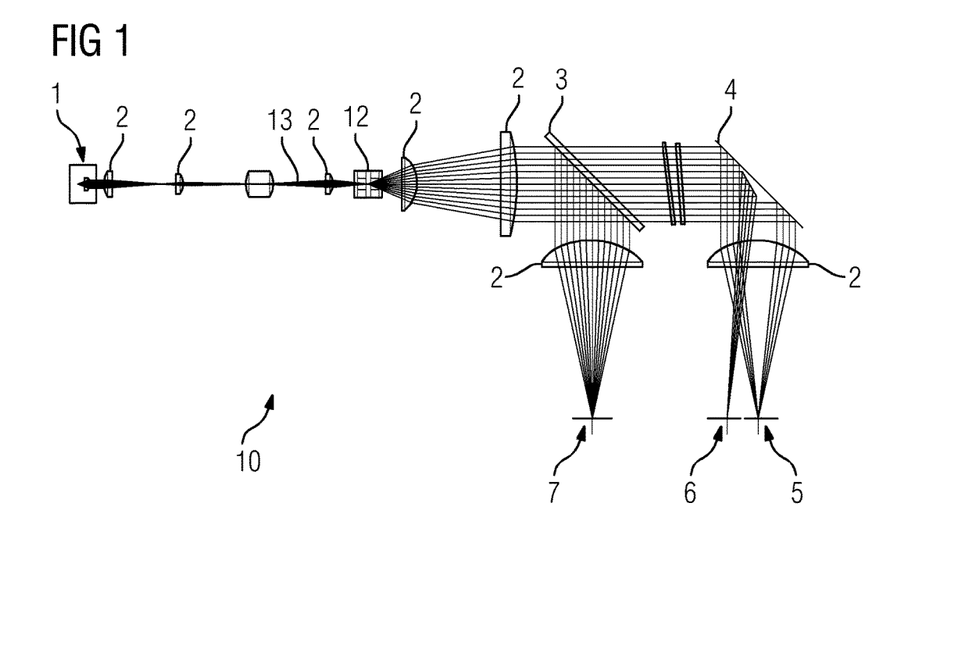
FIG. 1 shows an optical analysis system according to the prior art.

FIG. 1 shows an optical analysis system 10, which generates, using a light source 1, for example a laser, an analysis beam 13, which is focused in various lenses 2 such that the analysis beam 13 has a focus in an organic dispersion 12, wherein subsequently further focusing of the beam is performed by further lenses 2, so that it is analyzable in a large area by way of a beam splitter 3, on the one hand, in a spectral sensor 7, for example a spectrometer, and far field diffraction pattern 5 and near field diffraction pattern 6 are each detectable in a sensor via the mirror 4. In this manner, an entire array of measured values, which is to be assigned to an optical feature of the organic dispersion 12, may be determined automatically.

Figure 2:
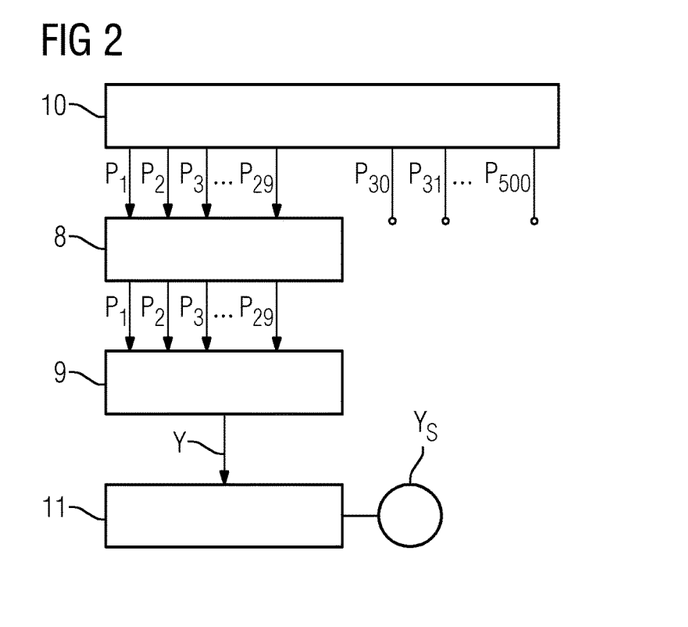
FIG. 2 shows a schematic illustration of a part of the data flow according to the analysis method according to the invention.

FIG. 2 shows the optical analysis system 10 with the output of measured values $P_i$, wherein i can run from i=1 to 500 and is used for consecutive numbering of the optical features. In this exemplary embodiment, the measured values $P_1$ to $P_{29}$ from the optical analysis method are processed in downstream data processing 8, which can be performed in a computer, for example, so that the measured values $P_1$ are usable in a multivariate analysis. The multivariate analysis consists of executing an exemplary embodiment of an analysis method according to the invention and determining a classification index Y, which can be assigned to the organic dispersion 12 from FIG. 1.

The classification index Y can be output in this case, for example, together with a threshold value $Y_S$, so that it is apparent for the operator of the optical analysis system 10 how a classification can be performed. However, this relates not only to a classification assistance in this case, in which a classification proposal is output by the analysis method. This means that a classification proposal is possibly established by the system, specifically if the classification index Y is greater than or less than a threshold $Y_S$, but if, for example, a diagnosis of an illness is to be performed, it is always incumbent upon the physician of the patient who has provided the organic dispersion in the form of a blood sample to make the diagnosis of an existing illness or not. If the classification index Y is precisely at the threshold value $Y=Y_S$, the optical analysis system does not provide any classification assistance.

Figure 3:
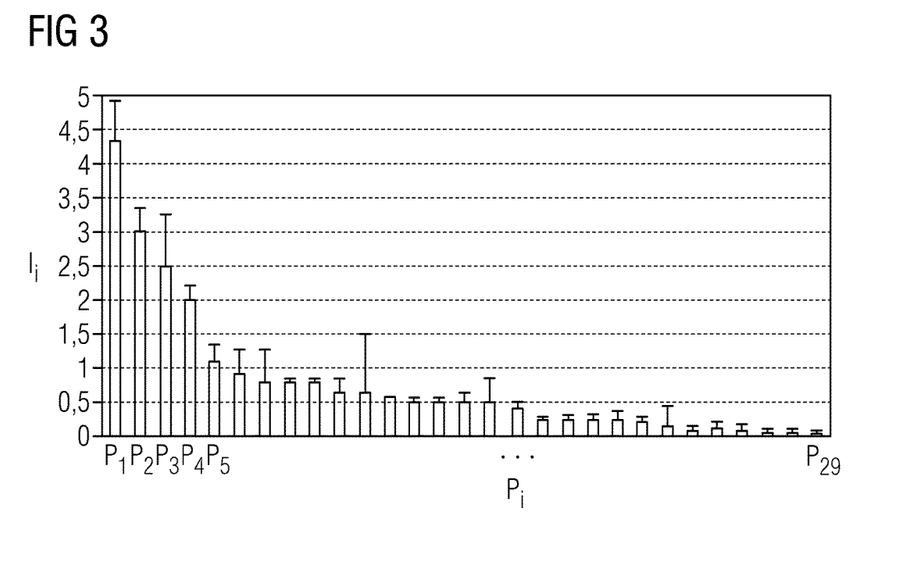
FIG. 3 shows an illustration of significance parameters for the associated measured value of a respective feature, ordered according to the absolute value thereof.

FIG. 3 shows a diagram having significance parameters $l_i$, wherein the significance parameters $l_i$ have been plotted over the respective measured value $P_i$. In this case, the measured values $P_i$ receive the running number i as a function of the absolute value of the associated significance parameter $l_i$. In other words, the sequence which is provided by the counter i also simultaneously reflects information about the information contribution of the measured value to the classification index.

The diagram shown in FIG. 3 relates to the same measured values $P_i$ which are also shown in FIG. 2.

Figure 4:
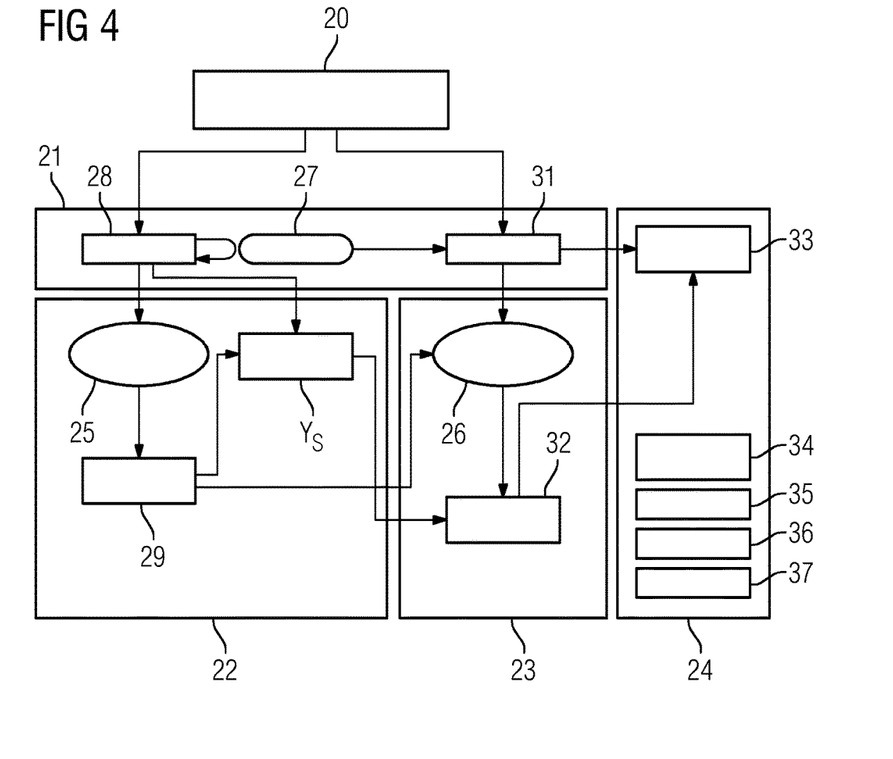
FIG. 4 shows a schematic diagram for the ascertainment of analysis parameters and a quality test for the analysis method.

FIG. 4 shows the example of a classification assistance for the malaria diagnosis, in which the analysis parameters are to be found by checking the quality of the classification assistance.

The malaria diagnosis assistance 20 is based on a training phase 28 and a subsequent test phase 31. In this case, the test phase 31 enables the standardization 27 of the training phase 28.

Firstly, the training 22 is begun on the basis of a value allocation 25 for the analysis parameters $Y_s$, $E_i$, $l_i$, $\sigma_i$, wherein a probability distribution of the classification index is generated on the basis of calibration data and a scaling is performed on the basis of this probability distribution, which enables a threshold $Y_s$ to be specified. If the scaling 29 was successful, the value allocation of the analysis parameters $Y_s$, $E_i$, $l_i$, $\sigma_i$ is thus retained, to be used in the analysis method.

In a second phase, the prediction 23, a test is performed on the basis of test data, which preferably are not part of the calibration data, but rather have been taken from another data set or another examination or the like.

On the basis of the found set of analysis parameters $Y_s$, $E_i$, $l_i$, $\sigma_i$, which in particular include the significance parameters $l_i$, classifications of test dispersions are performed, for which unambiguous classifications are already provided on the basis of the calibration data.

The classification 32 is the classification which can be assigned to the analysis method.

In the exemplary embodiment, the sensitivity and specificity are observed, to establish the classification accuracy, or in the case of a malaria classification assistance, the diagnosis accuracy, respectively.

The specificity is defined as the probability of a negative diagnosis, supposing that this classification is correct.

Sensitivity is defined as the probability of a positive classification, supposing that this classification is correct.

The correctness is established in the case of sensitivity and also in the case of sensitivity using the calibration data in a comparison.

In addition, other criteria are also to be taken into consideration, which can possibly be used alternatively or optionally, namely a canonical correlation 34, Wilks's lambda 35, fit parameter chi$^2$ 36, or a P-value 37 observation.

After the quality control 24, it can be decided whether the analysis method can offer an efficient classification rule, which meets the quality standards of medical analysis systems.

Figure 5:
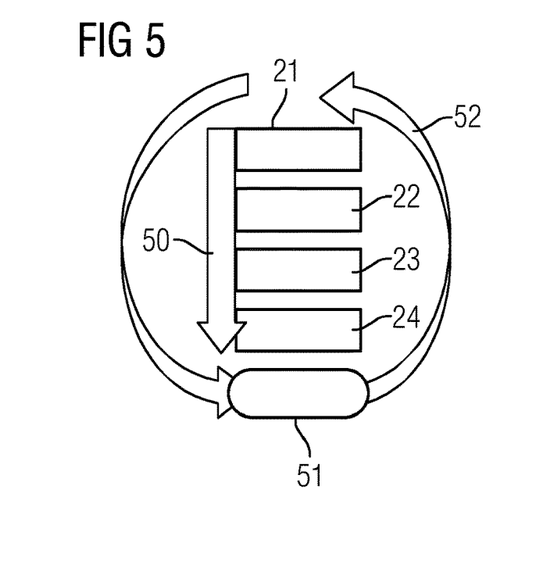
FIG. 5 shows a schematic illustration of program loops to improve the classification assistance.

FIG. 5 shows which steps of the steps known from FIG. 4 are to be reproduced.

The processing sequence 50 having the steps of resampling 21, training 22, prediction 23, and the quality control 24 can be repeated several hundred times, also thousands of times, typically precisely 1000 times, if personal computers are used.

If the analysis parameters found, in particular the significance parameters $l_i$, cannot be optimized further, the inner loop thus terminates with the processing sequence 50. The inner loop can propose a classification rule upon each execution. This is accordingly true upon the execution of the outer loop 52.

A query 51 is then performed as to whether a significance parameter $l_i$ is sufficiently small that it cannot contribute usable information to the classification index. If such a significance parameter $l_i$ is found, all analysis parameters which are associated with the respective optical measured value are thus not considered further, these include the standard deviation $\sigma_i$, the mean value $E_i$, and the significance parameter $l_i$ of the irrelevant optical feature.

If it was recognized, for example, that the number of fragments in the dispersion is unimportant for the malaria diagnosis, the significance parameter, which can be $l_{28}$, for example, could thus have assumed a value which is very close to zero. Therefore, the number of fragments is subsequently no longer used for the malaria diagnosis, in that the standard deviation $\sigma_{28}$, the mean value $E_{28}$, and the significance parameter $l_{28}$ are no longer taken into consideration. This can be achieved in a computer program in that $l_{28}$ is set to zero ($l_{28}=0$). The number n is reduced by one, whereby proceeding from n=29, for example, only n=28 optical features are still taken into consideration. In this case, the optical feature i=29 would receive the counter number 28, whereby the renewed start 52 of the outer loop can now be continued using 28 optical measured values.

Figure 6:
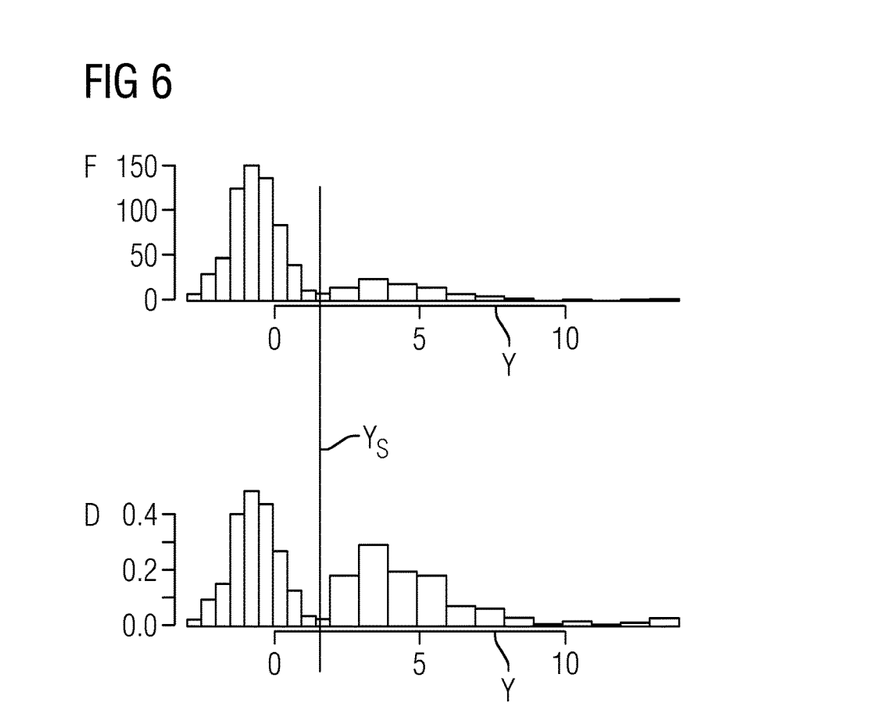
FIG. 6 shows two graphic representations for use in the discrimination analysis.

FIG. 6 shows two diagrams, wherein, in the upper diagram, the frequency of classification indices Y for a negative classification (narrow bars) and a positive classification (wide bars) are plotted over the classification index Y. It is apparent from the upper diagram that significantly fewer data sets are available for the positive classification than for a negative classification.

Furthermore, the knowledge of the actually provided classification is incorporated into the diagram insofar as known positive classifications are identified in the distribution using wide bars and negative classifications are shown in a distribution using narrow bars.

To go from the upper diagram to the lower diagram, the two distributions of different classifications were considered as a probability density distribution, and scaled accordingly therefrom. This scaling can set the surface area of the respective distributions to one, for example. Other scalings are possibly also advantageous. The scalings ensure that the different number of classifications in the calibration data does not have any influence on the classification rule to be determined.

Ideally, a significant separation would be desired between the probability density distributions D shown. In this manner, a threshold $Y_s$ would be determinable very easily, specifically in that $Y_s$ would be established between the value ranges of the two distributions. In the present case of the malaria diagnosis, it behaves so that the probability of an incorrect classification is possible for a range around the established threshold $Y_s$, because the classification index Y only has inadequate informative power in this range. The closer the classification index Y at a test dispersion is to the threshold value $Y_s$, the more probable is an incorrect classification.

A discrimination analysis of the distributions provided in FIG. 6 results in an establishment of the analysis parameters as specified in the following table for the analysis method for malaria diagnosis assistance. The number of the summands for determining the classification index is 29 and is identical to the number of optical features to be considered, which actually play a role in the test of the test dispersion. In fact, it began with 500 optical features, wherein 471 thereof proved to have a very small significance parameter $l_i$ in the course of the application of the ascertainment method and were removed from the set of the features i to be considered. The analysis parameters $l_i$, $E_i$, $\sigma_i$ of the remaining 29 optical features i read:

TABLE 1

| i | $l_i$ | $E_i$ | $\sigma_i$ |
|---|---|---|---|
| 1 | 0.0243143292327641 | 3.85878279704797 | 0.996350482855477 |
| 2 | 1.05744699221905 | 86.2085734326568 | 12.953846866348 |
| 3 | 1.3620780210087 | 31.3808859769373 | 2.65337438754902 |
| 4 | 0.298681341952128 | 16.7073148570111 | 3.05622820486547 |
| 5 | 0.039685909568696 | 3.18916825922509 | 0.610392795099183 |
| 6 | 0.802606052864478 | 22.4169387250923 | 6.67725822054997 |
| 7 | 0.013290099049454 | 1.80846317896679 | 0.490486418856065 |
| 8 | 0.172647099054505 | 0.602234248154981 | 0.216930342394397 |
| 9 | 0.0796067332070757 | 7.38290569464945 | 11.6539118822964 |
| 10 | 0.197381907473051 | 4.55739805811808 | 10.0180223771838 |
| 11 | 0.399165319578081 | 19.4079367287823 | 22.1428759582116 |
| 12 | 0.0494342161138479 | 1.24748103597786 | 2.31647351118736 |
| 13 | 1.44026210168956 | 26.9894740940959 | 5.0938073590873 |
| 14 | 0.520893299030793 | 4.28650641605166 | 1.07368357499902 |
| 15 | 0.284411335456635 | 16.4872902721402 | 12.5135939166568 |
| 16 | 0.531892835621228 | 7.23708487084871 | 8.95211789259242 |
| 17 | 0.698987246767777 | 336.37508399262 | 233.481906156752 |
| 18 | 0.488427163694765 | 9.19492226291513 | 2.00576799720274 |
| 19 | 0.683216666590792 | 53.4022117638376 | 11.7120398800053 |
| 20 | 2.39463588229883 | 23.307653449262 | 2.81445425488391 |
| 21 | 0.493291518472633 | 5.742889099631 | 0.731852460724153 |
| 22 | 0.199742256744743 | 1.95712033394834 | 0.25494636006376 |
| 23 | 1.76951528599063 | 0.839687189114391 | 0.161239146887579 |
| 24 | 0.0918169689792613 | 1.37246023431734 | 0.00515681120954237 |
| 25 | 2.99867547853134 | 34.8957316577491 | 5.81915230603462 |
| 26 | 2.46145277256995 | 17.5466706845018 | 3.58836148561811 |
| 27 | 0.0213275666681148 | 8.33807254059041 | 7.74938961818539 |
| 28 | 0.477404018065088 | 0.0352406872693727 | 0.136793871627217 |
| 29 | 0272433630134861 | 0.016729979704797 | 0.0197033898754757 |

The above table lists the analysis parameters $l_i$, $E_i$, $\sigma_i$, wherein both the associated measured value $P_i$ and also the listed analysis parameters $l_i$, $E_i$, $\sigma_i$ are assigned to the respective optical feature i, and wherein the parameter i is to be understood as the number of the respective optical feature.

TABLE 2

| i | $P_i$ | ADVIA parameter/optical feature | Definition of the measured value $P_i$ for the respective feature i |
|---|---|---|---|
| 1 | $P_1$ | RBC | Count of the red blood cells from the RBC/PLT channel |
| 2 | $P_2$ | MCV | Mean cell volume of the counted red blood cells (RBC) |
| 3 | $P_3$ | CHCM | Mean hemoglobin concentration (g/dL) of the cells (from RBC) |
| 4 | $P_4$ | RDW | Density distribution breadth of the red blood cells (from RBC) |
| 5 | $P_5$ | HDW | Breadth of the hemoglobin density distribution (g/dL) |
| 6 | $P_6$ | plat_mode | PLT mode |
| 7 | $P_7$ | mu_fit | μ-FIT |
| 8 | $P_8$ | sig_fit | σ-FIT |
| 9 | $P_9$ | micro_pcnt | Number of the RBC cells in percent having fewer than 60 fL |
| 10 | $P_{10}$ | macro_pcnt | Number of the RBC cells in percent having more than 120 fL |
| 11 | $P_{11}$ | hypo_pcnt | Number of the red blood cells in percent having a hemoglobin concentration of less than 28 g/dL |
| 12 | $P_{12}$ | hyper_pcnt | Number of the red blood cells in percent having a hemoglobin concentration of less than 41 g/dL |
| 13 | P13 | H_mean | Mean value of the hemoglobin concentration in picograms |
| 14 | P14 | H_deviation | Breadth of the hemoglobin content distribution in picograms |
| 15 | P15 | VHC_covar | Covariance of the hemoglobin density distribution |
| 16 | P16 | MN_PMN_valley | The BASO MN/PMN minimum as a depression between the MN and PMN clusters of the BASO cytogram |

TABLE 2-continued

| i | $P_i$ | ADVIA parameter/optical feature | Definition of the measured value $P_i$ for the respective feature i |
|---|---|---|---|
| 17 | P17 | PLT | Count of the recognized blood platelets |
| 18 | P18 | MPV | Mean blood platelet volume |
| 19 | P19 | PDW | Blood platelet distribution breadth |
| 20 | P20 | MPC | Mean blood platelet component concentration |
| 21 | P21 | PCDW | Distribution breadth of the blood platelet component concentration |
| 22 | P22 | MPM | Mean blood platelet dry mass |
| 23 | P23 | PMDW | Distribution depth of the blood platelet dry mass |
| 24 | P24 | PLT_Mean_n | Mean of a refractive index of the blood platelets (from PLT measurement) |
| 25 | P25 | PLT_Mean_X | Mean value of the diffraction deflection in X direction |
| 26 | P26 | PLT_Mean_Y | Mean value of the diffraction deflection in Y direction |
| 27 | P27 | Large_PLT | Large blood platelets (number) |
| 28 | P28 | RBC_Fragments | Number of the counted fragments in the PLT diffraction cytogram |
| 29 | P29 | RBC_Ghosts | Number of the events in the PLT diffraction cytogram without assignment |

ADVIA is a hematological analysis system having automated measured value ascertainment. The measured values $P_i$ are indicated with the respective abbreviation thereof, as are used in the so-called ADVIA export files, and are defined in the last column.

At this point, a reference is established to WO 00/58727 (PCT/US00/08512), the content of the disclosure of which is to be integrated by explicit reference into this intellectual property, in particular insofar as it relates to the measured values and optical features of the disclosed hematological analysis system used therein.

In the exemplary embodiment of the tables, a threshold $Y_s$=1.822 is proposed for the malaria diagnosis assistance. A diagnosis proposal can therefore be provided for each ascertained classification index of a blood sample with a small residual risk, namely with Y>1.822 a positive malaria finding and with Y<1.822 a negative malaria finding. Y=1.822 does not provide any assistance.

Figure 7:
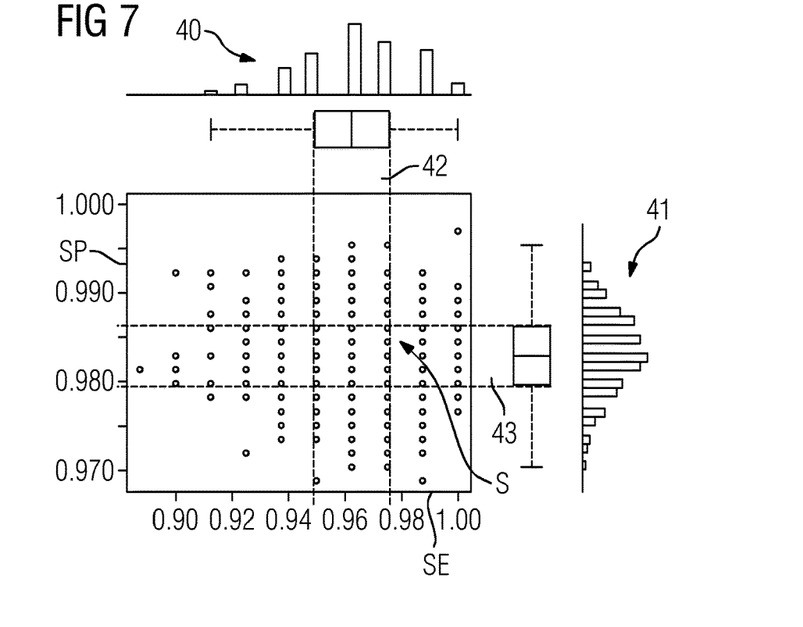
FIG. 7 shows a two-dimensional graphic illustration of the control and improvement of the classification assistance.

During the quality control 24 of the malaria diagnosis assistance, the specificity distribution 41 and the sensitivity distribution 40 were ascertained and plotted against one another in a two-dimensional graph. If the distributions are divided into 4 equal parts, the two middle quarters can thus be taken into consideration for this observation. In other words, the IQR 42 (interquartile range) of the distribution 40 and the IQR 43 of the distribution 41 are taken into consideration. To achieve the best results, it is recommended that classification rules be selected which are established within the intersection range S shown, to meet the highest medical requirements.

In the case of a simple mean value calculation, the sensitivity reaches 96.25%, and upon an observation of the IQR, it reaches a range from 59% to 97.5%. The specificity reaches an average of 98.29% and upon an observation of the IQR reaches a range from 97.98% to 89.60%. A correct classification is therefore extremely probable, wherein incorrect classification proposals can be excluded with only a small residual risk.

Figure 8:
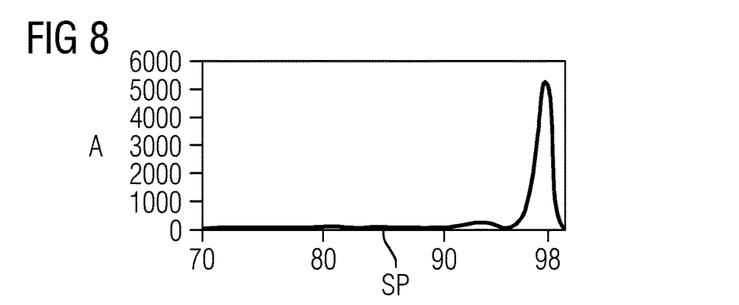
FIG. 8 shows a graphic illustration of a specificity histogram.
Figure 9:
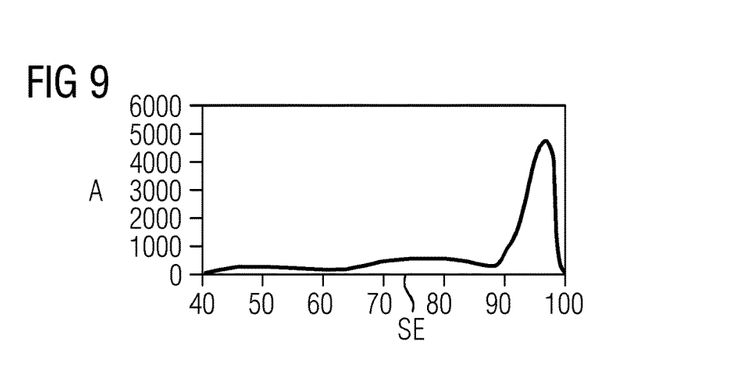
FIG. 9 shows an illustration of a sensitivity histogram.

FIG. 8 and FIG. 9 each show the number of established specificities or sensitivities in the form of histograms. The specificity $S_P$ and the sensitivity $S_E$ were already used as the bar diagram in FIG. 7.

In summary, the invention relates to an analysis method for classification assistance, an ascertainment method for determining analysis parameters $Y_S$, $E_i$, $l_i$, $\sigma_i$ for the analysis method, a computer program product, and an optical analysis system for classification assistance, in which, based on first and second calibration data, analysis parameters $Y_S$, $E_i$, $l_i$, $\sigma_i$ can be established, which provide a classification assistance according to rules of discrimination analysis, which, on the basis of measured values $P_i$ of optical features i, in particular organic dispersions, enable the information content thereof for the classification, in particular illness diagnoses, a classification proposal or diagnosis proposal in comparison to a threshold $Y_S$.

What is claimed is:

1. An analysis method for classification assistance having the following steps:
    focusing an analysis beam from a light source into a test dispersion to be classified;
    sensing the analysis beam extending through the test dispersion for optical features (i) of the test dispersion;
    ascertaining measured values ($P_i$) for the optical features (i) of the test dispersion to be classified,
    wherein the test dispersion is formed from a dispersion medium comprising a dispersed phase, and the dispersed phase has cells or cell components of organic materials,
    calculating a classification index (Y), defined by $$Y = \sum_{i=1}^{n} l_i * (P_i - E_i)/\sigma_i$$

wherein the classification index (Y) is dependent on a number (n) of the optical features (i) of the test dispersion, a significance parameter ($l_i$) of the respective optical feature (i), a mean value ($E_i$) of the respective optical feature (i), and a standard deviation ($\sigma_i$) of the respective optical feature (i);
    wherein the significance parameter ($l_i$) of the respective optical feature (i) indicates an extent to which a measured value ($P_i$) of the respective optical feature (i) has an effect on the classification index (Y);
    wherein at least two optical features (i) are taken into consideration for the calculation of the classification index (Y):

$$Y(n=2)=l_1*(P_1-E_1)/\sigma_1+l_2*(P_2-E_2)/\sigma_2,$$

wherein n=2 and a first optical feature is a measure of optical scattering in a transverse X direction in relation to the analysis beam, and a second optical feature is a measure of optical scattering in a Y direction, which is perpendicular to the X direction and also perpendicular to the analysis beam, and wherein the analysis beam extends through the test dispersion; and
    providing a diagnosis proposal based on the classification index that indicates whether the test dispersion originates from a sick patient, a healthy patient, or cannot be determined via a computer applying reduced computing power in response to usage of the significance parameter ($l_i$) of the respective optical feature (i).

2. The analysis method as claimed in claim 1, wherein the mean value ($E_i$) of the optical feature (i) and the standard deviation ($\sigma_i$) of the optical feature (i) were ascertained on the basis of first calibration data, wherein the first calibration data are derived from dispersions having a negative classification, the negative classification indicating a negative diagnosis, and second calibration data, wherein the second calibration data are derived from dispersions having a positive classification, the positive classification indicating a deficiency, a parasitic infestation, or a nonnormal state.

3. The analysis method as claimed in claim 2, wherein the significance parameters ($I_i$) are derived from the first calibration data and from the second calibration data by means of a discrimination analysis, wherein a Bayesian theory is used in the discrimination analysis.

4. The analysis method as claimed in claim 3, wherein, based on a first mean classification index ($Y_1$) of the first calibration data and a second mean classification index ($Y_2$) of the second calibration data, a threshold value ($Y_S$) is usable for the classification assistance, wherein $Y>Y_S$ is assigned to positive classification and $Y<Y_S$ is assigned to negative classification.

5. The analysis method as claimed in claim 4, wherein a positive classification indicates a presence of a deficiency, a parasitic infestation, or a nonnormal state, wherein the deficiency is an anemia.

6. The analysis method as claimed in claim 5 wherein the deficiency is a Mediterranean anemia or a sickle-cell anemia.

7. The analysis method as claimed in claim 5 wherein the parasitic infestation is a leishmaniasis.

8. The analysis method as claimed in claim 4 wherein the first mean classification index ($Y_1$) comprises a first focal point, and the second mean classification index ($Y_2$) comprises a second focal point.

9. The analysis method as claimed in claim 2 including an ascertaining step for determining analysis parameters ($Y_S$, $E_i$, $I_i$, $\sigma_i$), wherein for an established number (n) of optical features (i), the analysis parameters ($Y_S$, $E_i$, $I_i$, $\sigma_i$) of the standard deviation ($\sigma_i$), the mean value ($E_i$), and the significance parameters ($I_i$) are ascertained based on the first and the second calibration data.

10. The analysis method as claimed in claim 9, wherein at least one first control parameter, comprising a minimum or a fit parameter, is calculated based on the analysis parameters ($Y_S$, $E_i$, $I_i$, $\sigma_i$) to evaluate the classification assistance.

11. The analysis method as claimed in claim 10, wherein at least a part of the analysis parameters ($Y_S$, $E_i$, $I_i$, $\sigma_i$) is adapted after an evaluation by the first control parameter, wherein an adaptation of the at least one analysis parameter ($Y_S$, $E_i$, $I_i$, $\sigma_i$) and the evaluation of the classification assistance are executable alternately until an improvement is no longer possible or desirable.

12. The analysis method as claimed in claim 11, wherein the at least one part of the analysis parameters ($Y_S$, $E_i$, $I_i$, $\sigma_i$) is the significance parameters ($I_i$) or the threshold value ($Y_S$).

13. The analysis method as claimed in claim 11, wherein as soon as an improvement is no longer possible or desired, the analysis method is executable again using a reduced number of optical features (i), wherein the analysis parameters ($Y_S$, $E_i$, $I_i$, $\sigma_i$) of one nonsignificant optical feature (i) or multiple nonsignificant features (i) are no longer taken into consideration, wherein a lack of significance of an optical feature (i) is determined on the basis of the significance parameter ($I_i$).

14. The analysis method as claimed in claim 13, wherein a lack of significance exists if the influence of the optical feature (i) on the classification index (Y) is small.

15. A non-transitory computer readable storage medium comprising instructions configured to cause the computer to execute the analysis method as claimed in claim 9.

16. An optical analysis system for carrying out the analysis method as claimed in claim 9, the optical analysis system comprising:
    a light source for providing an analysis beam directed at an organic dispersion;
    a plurality of lenses for focusing the analysis beam before and after the organic dispersion;
    a beam splitter for splitting the analysis beam or a mirror for reflecting the analysis beam or both;
    one or more spectral sensors positioned to receive the analysis beam from the beam splitter, the mirror, or both; and
    the computer.

17. A non-transitory computer readable storage medium comprising instructions configured to cause the computer to execute the analysis method as claimed in claim 1.

18. An optical analysis system for carrying out the analysis method as claimed in claim 1, the optical analysis system comprising:
    a light source for providing an analysis beam directed at an organic dispersion;
    a plurality of lenses for focusing the analysis beam before and after the organic dispersion;
    a beam splitter for splitting the analysis beam or a mirror for reflecting the analysis beam or both;
    one or more spectral sensors positioned to receive the analysis beam from the beam splitter, the mirror, or both; and
    the computer.

19. The analysis method as claimed in claim 1 wherein the dispersion medium comprises blood plasma.

\* \* \* \* \*

UNITED STATES PATENT AND TRADEMARK OFFICE
CERTIFICATE OF CORRECTION

PATENT NO. : 10,401,275 B2  
APPLICATION NO. : 14/912876  
DATED : September 3, 2019  
INVENTOR(S) : Barbara Kavsek et al.

Page 1 of 1

It is certified that error appears in the above-identified patent and that said Letters Patent is hereby corrected as shown below:

On the Title Page

In Column 2, in the Abstract, on Lines 3 and 6, the two occurrences of the parameter "$I_i$" should each be --$l_i$--;

In the Claims

In Column 15, on Lines 29, 30, and 32, the three occurrences of the parameter "$I_i$" should each be --$l_i$--;

In Column 15, on Line 37, the parameter "$I_i$" should be --$l_i$--;

In Column 15, on Lines 39 and 42, the two occurrences of the parameter "$I_i$" should each be --$l_i$--;

In Column 15, on Lines 46 and 47, the two occurrences of the parameter "$I_i$" should each be --$l_i$--; and In Column 16, on Lines 5 and 9, the two occurrences of the parameter "$I_i$" should each be --$l_i$--.

Signed and Sealed this  
Twenty-first Day of April, 2020

Andrei Iancu  
*Director of the United States Patent and Trademark Office*